United States Patent
Son et al.

(10) Patent No.: US 10,793,687 B2
(45) Date of Patent: Oct. 6, 2020

(54) HARD CAPSULE HAVING IMPROVED THICKNESS UNIFORMITY

(71) Applicant: SAMSUNG FINE CHEMICALS CO., LTD., Ulsan (KR)

(72) Inventors: Jin Ryul Son, Incheon (KR); Kil Seuk Byun, Yongin-si (KR)

(73) Assignee: LOTTE FINE CHEMICAL CO., LTD., Ulsan (KR)

( * ) Notice: Subject to any disclaimer, the term of this patent is extended or adjusted under 35 U.S.C. 154(b) by 228 days.

(21) Appl. No.: 14/443,485

(22) PCT Filed: Jul. 16, 2013

(86) PCT No.: PCT/KR2013/006340
§ 371 (c)(1),
(2) Date: May 18, 2015

(87) PCT Pub. No.: WO2014/088178
PCT Pub. Date: Jun. 12, 2014

(65) Prior Publication Data
US 2015/0291744 A1    Oct. 15, 2015

(30) Foreign Application Priority Data
Dec. 5, 2012 (KR) .................. 10-2012-0140551

(51) Int. Cl.
*B65D 65/46* (2006.01)
*C08J 5/00* (2006.01)
(Continued)

(52) U.S. Cl.
CPC .............. *C08J 5/00* (2013.01); *A61K 9/4816* (2013.01); *B65D 65/46* (2013.01); *A61J 3/071* (2013.01);
(Continued)

(58) Field of Classification Search
CPC .......... A61K 9/48; A61K 9/2866; A61K 9/00; A61K 9/4816; B65D 65/46; A61J 3/07
(Continued)

(56) References Cited

U.S. PATENT DOCUMENTS 3,493,407 A * 2/1970 Greminger, Jr. ...... C08B 11/193
                                                                  106/194.1
4,402,692 A * 9/1983 Takagishi ............... A61K 9/025
                                                                  424/436
(Continued)

FOREIGN PATENT DOCUMENTS

| CN | 1326733 A | 12/2001 |
| CN | 1745745 A | 3/2006 |

(Continued)

OTHER PUBLICATIONS

Dow-Cellulose Ethers: Technical Overiew and Product Guide, http://www.dowconstructionchemicals.com/na/en/pdfs/832-00226.pdf Re May 2012.*
(Continued)

*Primary Examiner* — Lee E Sanderson
*Assistant Examiner* — Michael C Romanowski
(74) *Attorney, Agent, or Firm* — Cantor Colburn LLP

(57) ABSTRACT

Provided is a hard capsule. The provided hard capsule includes water-soluble cellulose ether, about 0.5 parts by weight to about 1.5 parts by weight of a gelation agent based on 100 parts by weight of the water-soluble cellulose ether, and about 0 parts by weight to about 0.3 parts by weight of a gelation aid based on 100 parts by weight of the water-soluble cellulose ether, wherein the hard capsule comprises a body and a cap that seals the body, and a ratio of a maximum thickness to a minimum thickness of the body and the cap is each 2.5 or less.

11 Claims, 2 Drawing Sheets

(51) Int. Cl.
*A61K 9/48* (2006.01)
*A61J 3/07* (2006.01)

(52) U.S. Cl.
CPC ........ *C08J 2301/28* (2013.01); *C08J 2405/00* (2013.01)

(58) Field of Classification Search
USPC ............................................... 428/34.1, 34.7
See application file for complete search history.

(56) References Cited

U.S. PATENT DOCUMENTS

| | | | |
|---|---|---|---|
| 4,917,885 A | 4/1990 | Chiba et al. | |
| 6,410,050 B1 | 6/2002 | Yang | |
| 6,413,463 B1 * | 7/2002 | Yamamoto | A61K 9/4816 264/301 |
| 6,649,180 B1 * | 11/2003 | Matsuura | A61K 9/4816 424/402 |
| 2004/0022845 A1 | 2/2004 | Zhang | |
| 2010/0212261 A1 * | 8/2010 | Boldis | A61J 3/071 53/403 |

FOREIGN PATENT DOCUMENTS

| | | |
|---|---|---|
| CN | 101167705 A | 4/2008 |
| EP | 1029539 | 8/2000 |
| EP | 1849461 A1 | 10/2007 |
| EP | 2476439 A1 | 7/2012 |
| JP | 03009755 A | 1/1991 |
| JP | 2000136126 A | 5/2000 |
| JP | 2001245609 A | 9/2001 |
| JP | 2005187412 | 7/2005 |
| JP | 2005187412 A | 7/2005 |
| JP | 2010202550 A | 9/2010 |
| KR | 1020000057602 | 9/2000 |
| KR | 1020010033693 | 4/2001 |
| KR | 1020060103566 | 10/2006 |
| KR | 1020090057470 | 6/2009 |
| MX | 2009004434 A | 4/2009 |
| WO | 2006082842 A1 | 8/2006 |
| WO | 2007003113 A1 | 1/2007 |
| WO | 2011030952 | 3/2011 |
| WO | 2011155686 A1 | 12/2011 |
| WO | 2014088177 A1 | 6/2014 |

OTHER PUBLICATIONS

International Search Report—PCT/KR2013/006340 dated Oct. 24, 2013.
Written Opinion—PCT/KR2013/006340 dated Oct. 24, 2013.
Japanese Office Action for Application No. 2015546731 dated Jun. 8, 2017.

* cited by examiner

HARD CAPSULE HAVING IMPROVED THICKNESS UNIFORMITY

TECHNICAL FIELD

The present invention relates to a hard capsule, and more particularly, to a hard capsule having improved thickness uniformity.

BACKGROUND ART

In general, hard capsules are prepared by using gelatin derived from bovine animal or swine.

Gelatin-containing aqueous compositions are prepared in a relatively short period of time due to the possibility of the direct dissolution of gelatin in high-temperature water (for example, 60 ☐), and when a mold pin is immersed therein and then taken therefrom to dry the gelatin-containing aqueous compositions coated on the mold pin, the drying time is short, the obtained hard capsule may have excellent elasticity, glossiness, and disintegrability, and the production yield of the hard capsule is very high. However, concerns regarding mad cow disease have limited the use of gelatin capsules, and accordingly, capsules prepared by using a plant-based cellulose ether, instead of the gelatin, are getting much attention.

However, although cellulose ether dissolves in room temperature (25° C.) water, as soon as the cellulose ether is added to water, most of the cellulose ether aggregates to form an aggregate, thus requiring a long time for complete dissolution. To prevent this problem, when an aqueous composition for preparing a hard capsule is prepared, the cellulose ether is added to high temperature (for example, 80° C. or higher) water to prevent the aggregation and then dispersed well to prepare a dispersion. Then, the dispersion is naturally cooled down to a first temperature (for example, about 40° C. to about 50° C.) to dissolve the dispersed cellulose ether in water. Thereafter, the resultant is heated to a second temperature (for example, about 55° C. to about 65° C.), and then a gelation agent and optionally a gelation aid are added to the resultant. In this regard, the heating of the resultant to the second temperature is performed to prevent solidification of the gelation agent and the gelation aid. However, cellulose ether may not be completely dissolved in water at the second temperature, and thus an aqueous composition and a final hard capsule, including the cellulose ether, may have the following disadvantages:

(1) the aqueous composition may have a varying viscosity according to location and may also undergo a layer-separation during a long-term storage;

(2) a degree of mixing of a cellulose ether and a gelation agent (and optionally, a gelation aid) in the aqueous composition may decrease, thereby requiring more gelation agent (and optionally, a gelation aid) to be added thereto. However, due to the addition of more gelation agent, a haze phenomenon occurs on a capsule surface;

(3) the aqueous composition may have a low filtering efficiency in a subsequent filtering process for removing foreign materials (for example, fiber) therefrom;

(4) even after the filtering process, foreign materials may remain in the aqueous composition to deteriorate the performance of a capsulation agent and/or a capsulation aid, leading to a decrease in capsule moldability or formability;

(5) During a mold pin dipping process of a capsule molding process, when the mold pin is inserted into the aqueous composition and then taken out therefrom, the aqueous composition coated on the mold pin sags towards the bottom of the mold pin and when the mold pin is inverted, the aqueous composition that sagged towards the bottom of the mold pin becomes concentrated at one portion, generating non-uniformity in a thickness of a capsule film after drying, thereby causing wrinkle faults on that portion after the drying;

(6) when a drying process is performed to evaporate water in the aqueous composition coated on a substrate (for example, a mold pin) in a capsule molding process, a drying rate of the aqueous composition is low;

(7) the preparation time and drying time of the aqueous composition are long, and thus, the production yield of a hard capsule is low; and (8) foreign materials remaining in the aqueous composition are included in a hard capsule, which is a final product, and due to the included foreign materials, the quality (elasticity, glossiness, disintegrability, or the like) of the hard capsule decreases, and it is difficult to keep the quality of a hard capsule constant for all production lots.

DETAILED DESCRIPTION OF THE INVENTIVE CONCEPT

Technical Problem

The present invention provides a hard capsule having improved thickness uniformity.

Technical Solution

According to an aspect of the present invention, there is provided a hard capsule including water-soluble cellulose ether, about 0.5 parts by weight to about 1.5 parts by weight of a gelation agent based on 100 parts by weight of the water-soluble cellulose ether, and about 0 parts by weight to about 0.3 parts by weight of a gelation aid based on 100 parts by weight of the water-soluble cellulose ether, wherein the hard capsule comprises a body, and a cap that seals the body, and a ratio of a maximum thickness to a minimum thickness of the body and the cap is each 2.5 or less.

The hard capsule of claim 1, wherein

The body and the cap each may include a top portion, a shoulder portion, a dome portion, and a cutting edge portion, wherein thicknesses for portions of the body and the cap may be each independently, the top portion from about 130 μm to about 180 μm, the shoulder portion from about 50 μm to about 100 μm, the dome portion from about 100 μm to about 120 μm, and the cutting edge portion from about 90 μm to about 110 μm The water-soluble cellulose ether may include hydroxypropyl methylcellulose (HPMC), hydroxyethyl methylcellulose (HEMC), methylcellulose (MC), or a mixture of two or more of these.

The gelation agent may include Carrageenan, Gellan gum, Xanthan gum, Pectin, or a mixture of two or more of these.

The gelation aid may include potassium chloride, potassium acetate, calcium chloride, or a mixture of two or more of these.

The hard capsule may further include 0 parts by weight to about 5.0 parts by weight of other additives based on 100 parts by weight of the water-soluble cellulose ether.

The other additives may include a plasticizer, an emulsifier, or a mixture of these.

Advantageous Effects

A hard capsule according to an embodiment of the present invention includes a small amount of a gelation agent (and optionally a gelation aid), and may have improved thickness uniformity.

BEST MODE

Hereinafter, a hard capsule according to an embodiment of the present invention is described in detail.

A hard capsule according to an embodiment of the present invention includes a water-soluble cellulose ether, about 0.5 parts by weight to about 1.5 parts by weight of a gelation agent based on 100 parts by weight of the water-soluble cellulose ether, and 0 parts by weight to about 0.3 parts by weight of a gelation aid based on 100 parts by weight of the water-soluble cellulose ether, wherein the hard capsule includes a body and a cap that seals the body, wherein the body and the cap each have a ratio of a maximum thickness to a minimum thickness of 2.5 or less. As used herein, the term "minimum thickness" refers to a thickness having the minimum value among thicknesses of the body or the cap of the hard capsule at all measurable locations, and "maximum thickness" refers to a thickness having the maximum value among thicknesses of the body or the cap of the hard capsule at all measurable locations.

When the amount of the gelation agent is less than 0.5 parts by weight based on 100 parts by weight of the water-soluble cellulose ether, capsule moldability decreases and when the amount of the gelation agent exceeds 1.5 parts by weight, not only does manufacturing cost of the hard capsule increase, but also a hard capsule having a low elongation at break, high brittleness, and a non-uniform film thickness is obtained.

When the amount of the gelation aid exceeds 0.3 parts by weight based on 100 parts by weight of the water-soluble cellulose ether, a hard capsule having a high haze and thus a low light transmittance is obtained.

The body and the cap may each have a ratio of the maximum thickness to the minimum thickness of between 1.5 and 2.5.

Hereinafter, the hard capsule is described in greater detail with reference to FIG. 1.

Figure 1:
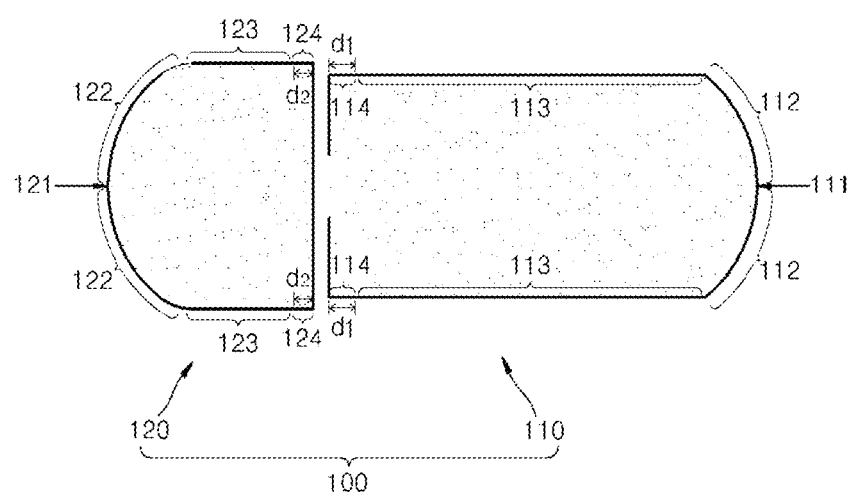
FIG. 1 is a side view of a hard capsule according to an embodiment of the present invention.

FIG. 1 is a side view of a hard capsule 100 according to an embodiment of the present invention Referring to FIG. 1, the hard capsule 100 includes a body 110 and a cap 120. In FIG. 1, the body 110 and the cap 120 are illustrated in a separated state.

The body 110 includes a top portion 111, a shoulder portion 112 that is radially extended from the top portion 111 as a reference point, wherein the shoulder portion 112 has an empty hemisphere form, a dome portion 113 that is coupled to an end of the shoulder portion 112, wherein the dome portion 113 has a cylindrical form, and a cutting edge portion 114 coupled to an end of the dome portion 113.

The cap 120 includes a top portion 121, a shoulder portion 122 that is radially extended from the top portion 121 as a reference point, wherein the shoulder portion 122 has an empty hemisphere form, a dome portion 123 that is coupled to an end of the shoulder portion 121, wherein the dome portion 123 has as cylindrical form, and a cutting edge portion 124 coupled to an end of the dome portion 123.

Thicknesses of portions of the body 110 and the cap 120 are each independently, the top portions 111 and 121 from about 130 μm to about 180 μm, the shoulder portions 112 and 122 from about 50 μm to about 100 μm, the dome portions 113 and 123 from about 100 μm to about 120 μm, and the cutting edge portions 114 and 124 from about 90 μm to about 110 μm.

The body 110 and the cap 120 may each independently have distances ($d_1$, $d_2$) from interfaces of the dome portions 113 and 123 and the cutting edge portions 114 and 124 to the ends of the cutting edge portions 114 and 124 of 1 mm or less.

The water-soluble cellulose ether is a major component of the hard capsule. The water-soluble cellulose ether is derived from a plant-based cellulose, and is advantageous for being harmless to the human body. The term "cellulose ether" as used herein refers to a cellulose derivative prepared by etherifying a hydroxy group of cellulose by using an etherifying agent.

The water-soluble cellulose ether may include hydroxypropyl methylcellulose (HPMC), hydroxyethyl methylcellulose (HEMC), methylcellulose (MC), or a mixture of two or more of these.

The gelation agent performs a role of gelling an aqueous composition for preparing a hard capsule, which is described below.

The gelation agent may include a water-soluble gum.

The water-soluble gum may include Carrageenan, Gellan gum, Xanthan gum, Pectin, or a mixture of two or more of these.

The gelation aid supplements the gelation ability of the gelation agent to perform the role of improving capsule moldability of the aqueous composition for preparing a hard capsule.

The gelation aid may include potassium chloride, potassium acetate, calcium chloride, or a mixture of two or more of these.

The hard capsule may further include 0 parts by weight to about 5 parts by weight of other additives based on 100 parts by weight of the water-soluble cellulose ether.

The other additives may include a plasticizer, an emulsifier, or a mixture of two or more of these.

The plasticizer performs a role of improving film strength of the hard capsule.

The plasticizer may include glycerol, sorbitol, propylene glycol, polyethylene glycol or a mixture of two or more of these.

The amount of the plasticizer may be about 0 wt % to about 5.0 wt % of the aqueous composition for preparing a hard capsule. When the amount of the plasticizer is within this range, a hard capsule having a high elongation at break and transparency (hence, a low haze) may be obtained.

The emulsifier performs a role of improving capsule moldability of the aqueous composition for preparing a hard capsule.

The emulsifier may include sodium lauryl sulfate (SLS), sucrose esters of fatty acids, or a mixture of these.

The amount of the emulsifier may be about 0 wt % to about 1.0 wt % of the aqueous composition for preparing a hard capsule. When the amount of the emulsifier is within this range, a hard capsule having high quality and harmless to human body may be obtained.

When the amount of the other additives is within the range above (0 parts by weight to about 5 parts by weight), a hard capsule having excellent transparency, quality and safety in a human body may be obtained.

The hard capsule may be gastric juice soluble.

Hereinafter, a method of preparing the hard capsule is described in detail.

(Preparation of Aqueous Composition for Preparing a Hard Capsule)

The aqueous composition for preparing a hard capsule is prepared via a process for preparing a cellulose ether solution that includes water, an alcohol, and water-soluble cellulose ether, and is maintained at a first temperature (40° C. to 70° C.) that is higher than an atmospheric temperature (0° C. to 39° C.). In detail, the aqueous composition for preparing a hard capsule may be prepared via processes for mixing water and an alcohol to prepare an aqueous alcohol solution (S1), heating the aqueous alcohol solution (S2), dissolving water-soluble cellulose ether in the heated aqueous alcohol solution to prepare a cellulose ether solution (S3), aging the cellulose ether solution (S4), and adding a gelation agent to the resultant (S5).

In the process (S2), the heating of the aqueous alcohol solution may be performed from room temperature (20° C. to 30° C.) to a temperature of 40° C. to 70° C. The process (S2) is performed to allow the water-soluble cellulose ether to be dispersed well in the aqueous alcohol solution in the process (S3) so that the water-soluble cellulose ether is easily dissolved without aggregation. When the heating temperature is within this range, the gelation agent (and optionally, gelation aid) may have high capsule moldability without solidification, and an aqueous composition for preparing a hard capsule may be obtained that minimizes increases in the energy costs associated with inevitable heating.

The process (S3) may be performed by slowly adding the water-soluble cellulose ether to the heated aqueous alcohol solution while stirring (for example, 300 rpm).

However, the present invention is not limited thereto. For example, instead of the processes (S1 to S3), the water-soluble cellulose ether may be dissolved in water (or an alcohol) to prepare a first cellulose ether solution, and then an alcohol (or water) may be added to the first cellulose ether solution to prepare a second cellulose ether solution. Also, in this case, heated water and/or heated alcohol may be used in the preparation of the cellulose ether solution, or water-soluble cellulose ether may be dissolved in water (or an alcohol) to prepare a first cellulose ether solution, and then the first cellulose ether solution may be heated and an alcohol (or water) may be added thereto to prepare a second cellulose ether solution.

The aging process (S4) of the cellulose ether solution may be performed at a temperature of 40 to 70° C. for 2 to 12 hours. When the aging process (S4) is performed for this time range (hence, aging time), bubbles may be sufficiently removed from the resultant and a composition of the resultant may be uniform.

In the process (S4), a gelation aid and/or other additives (e.g., plasticizer, emulsifier, and the like) in addition to the gelation agent may be further added to the resultant.

At least one process of the processes (S1 to S5) may be performed while stirring.

The process (S5) may be additionally followed by removing bubbles from the aqueous composition for preparing a hard capsule. This process (S5) may be performed by stirring.

The aqueous composition for preparing a hard capsule prepared by the method above includes water-soluble cellulose ether, a gelation agent, alcohol, and water, wherein an amount of the gelation agent may be about 0.5 parts by weight to about 1.5 parts by weight based on 100 parts by weight of the water-soluble cellulose ether. When the amount of the gelation agent is less than 0.5 parts by weight based on 100 parts by weight of the water-soluble cellulose ether, the aqueous composition for preparing a hard capsule is not sufficiently gelled when being heated, and thus film moldability thereof decreases, and when the amount of the gelation agent exceeds 1.5 parts by weight, not only does manufacturing cost of the aqueous composition for preparing a hard capsule increase, but also viscosity and gelation ability of the aqueous composition for preparing a hard capsule increase excessively, thereby forming a hard capsule having a low elongation at break, high brittleness, and a non-uniform film thickness, wherein the non-uniform film thickness is due to a decrease in flowability of the aqueous composition for preparing a hard capsule in a hard capsule molding process.

Also, the aqueous composition for preparing a hard capsule may not include the gelation aid or may further include 0.3 parts by weight or less of the gelation aid based on 100 parts by weight of the water-soluble cellulose ether.

The aqueous composition for preparing a hard capsule may include about 10 wt % to about 25 wt % of the water-soluble cellulose ether.

When the amount of the water-soluble cellulose ether in the aqueous composition for preparing a hard capsule is within the range above (about 10 wt % to about 25 wt %), an aqueous composition for preparing a hard capsule having a suitable viscosity may be obtained such that bubbles generated therefrom are easily removed and a hard capsule having a suitable thickness may be obtained.

The aqueous composition for preparing a hard capsule may further include 0 parts by weight to about 5 parts by weight of other additives based on 100 parts by weight of the water-soluble cellulose ether.

The alcohol may help the water-soluble cellulose ether to be liquefied (i.e., dissolved) in the aqueous composition for preparing a hard capsule. This process is described in more detail as follows: when the water-soluble cellulose ether is added to room temperature (20° C. to 30° C.) water, a part of the water-soluble cellulose ether that directly contacts water dissolves but other parts of the water-soluble cellulose ether that do not directly contact water aggregate to form a lump, and when the water-soluble cellulose ether is added to high temperature (40° C. to 70° C.) water, even the part of the water-soluble cellulose ether that directly contacts water does not dissolve well. However, the alcohol is mixed with water to form an aqueous alcohol solution, and the water-soluble cellulose ether dissolves well not only in a room temperature (20° C. to 30° C.) aqueous alcohol solution but also in a high temperature (40° C. to 70° C.) aqueous alcohol solution.

The alcohol may include ethanol, methanol, isopropanol, butanol, or a mixture of two or more of these.

The aqueous composition for preparing a hard capsule may include about 5 wt % to about 30 wt % of the alcohol.

When the amount of the alcohol is within this range (about 5 wt % to about 30 wt %), solubility of the cellulose ether increases and an evaporation rate of the alcohol becomes suitable for a hard capsule preparation, and thus a smooth film without wrinkles may be obtained.

The functions, types, and the amounts of the water-soluble cellulose ether, the gelation agent, the gelation aid, the plasticizer, and the emulsifier are as described above, and thus explanations thereof will be omitted herein.

When the aqueous composition for preparing a hard capsule is heated to a capsule molding temperature (40° C. to 70° C.), the water-soluble cellulose ether may be completely dissolved. Due to the complete dissolution of the water-soluble cellulose ether, the aqueous composition for preparing a hard capsule may have the following advantages: a shorter preparation time; higher homogeneity, uniform viscosity and no layer-separation even during a period of long-term storage; uniform viscosity for all production lots; higher capsule moldability due to the absence of undissolved materials (for example, cellulose ether) that suppress performance of a gelation agent (and optionally, a gelation aid); reduction of the amount of a gelation agent (and optionally, gelation aid) added thereto due to a high degree of mixing of the cellulose ether and the gelation agent (and optionally, the gelation aid); a high filtering efficiency in a subsequent filtering process for removing foreign materials from the aqueous composition for preparing a hard capsule; a higher drying rate due to a solvent component (e.g., alcohol) when a drying process of the aqueous composition coated on a substrate (e.g., a mold pin) is performed in a capsule molding process; and a higher production yield of a hard capsule due to shorter preparation time and drying time of the aqueous composition for preparing a hard capsule.

Also, the aqueous composition for preparing a hard capsule includes a small amount of an expensive gelation agent and optionally includes a small amount of a cheap gelation aid that may supplement the gelation ability of the gelation agent such that the aqueous composition for preparing a hard capsule has a low manufacturing cost, high uniformity and gel strength, and a hard capsule having a low haze may be formed.

(Preparation of Hard Capsule)

The aqueous composition for preparing a hard capsule is coated on a substrate (a mold pin, a glass substrate, or the like) and then dried to prepare a hard capsule. For example, the hard capsule may be manufactured by immersing a room temperature (20° C. to 30° C.) mold pin in an aqueous composition for preparing a hard capsule heated to a high temperature (40° C. to 70° C.), taking out the mold pin from the aqueous composition to dry the aqueous composition coated on the mold pin.

The hard capsule is of high quality (elasticity, glossiness, disintegrability, and the like) due to the absence of foreign materials, such as fiber, in the aqueous composition for preparing a hard capsule, and the quality may be kept constant for all production lots.

Hereinafter, the present invention is described in greater detail with reference to Examples, but the present invention is not limited to the Examples.

Mode of the Inventive Concept

EXAMPLE

Examples 1 to 4 and Comparative Examples 1 and 2

Preparation of Aqueous Composition for Preparing a Hard Capsule

Ethanol was mixed with water (purified water) at ratios shown in Table 1 below to prepare aqueous ethanol solutions. Thereafter, each of the aqueous ethanol solutions was heated to a temperature shown in Table 1 below, and then hydroxypropyl methylcellulose (HPMC) (available from Samsung Fine Chemical Co., Ltd., AW4) was added to the aqueous ethanol solution in a ratio shown in Table 1 below and dissolved therein. Then, K-Carrageenan (available from Korea Carragheen Co., Ltd, HG404) as a gelation agent and potassium chloride as a gelation aid were added to the resultant at ratios shown in Table 1 below to obtain an aqueous composition for preparing a hard capsule.

TABLE 1

|  | Water (parts by weight*[1]) | Ethanol (parts by weight*[1]) | HPMC (parts by weight*[1]) | K-Carrageenan (parts by weight*[2]) | Potassium chloride (parts by weight*[2]) | Temperature of aqueous ethanol solution (° C.) |
|---|---|---|---|---|---|---|
| Example 1 | 65 | 15 | 20 | 1.5 | 0 | 60 |
| Example 2 | 65 | 15 | 20 | 1.0 | 0.05 | 60 |
| Example 3 | 65 | 15 | 20 | 0.7 | 0.2 | 60 |
| Example 4 | 65 | 15 | 20 | 0.5 | 0.3 | 60 |
| Comparative Example 1 | 80 | 0 | 20 | 1.0 | 0.5 | 60 |
| Comparative Example 2 | 80 | 0 | 20 | 0.5 | 0.3 | 60 |

*[1]Based on 100 parts by weight of (water + ethanol + HPMC)
*[2]Based on 100 parts by weight of HPMC (Preparation of Flat Film)

The each aqueous composition for preparing a hard capsule maintained at a temperature of 60° C. was coated on a glass substrate by using a film caster (self-manufactured by Samsung Fine Chemicals Co., Ltd). Then, the glass substrate coated with the aqueous composition for preparing a hard capsule was dried at room temperature (25° C.) for 24 hours to obtain a flat film having a thickness of 100 μm.

(Preparation of Hard Capsule)

Figure 2:
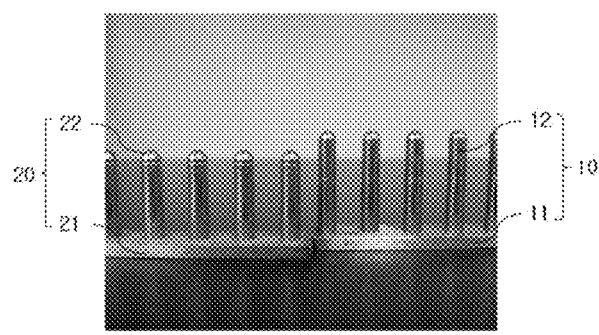
FIG. 2 is a photo image showing a mold pin for preparing a hard capsule of FIG. 1.

A room temperature (25° C.) metal mold pin (size 0) was gradually immersed in the each aqueous composition for preparing a hard capsule (a temperature of the composition: 55° C.) over three seconds to coat the each aqueous composition for preparing a hard capsule on the mold pin. Then, the mold pin was gradually taken out from the each aqueous composition for preparing a hard capsule over three seconds, maintained for 10 seconds, and then the mold pin was inverted. Then, the mold pin coated with the aqueous composition was put into a drying oven which was maintained at a temperature of 30° C. to dry the mold pin for 40 minutes and prepare a hard capsule. However, the aqueous composition for preparing a hard capsule prepared in Comparative Example 2 did not have sufficient gelation ability and thus, a hard capsule could not be formed. In this regard, as illustrated in FIG. 2, the mold pin is separated into a mold pin for a body 10 and a mold pin for a cap 20, and the experiment described above was repeated for two types of the mold pin 10 and 20 to prepare each of the body and the cap. In more detail, when each mold pin 10 and 20 was immersed in each aqueous composition for preparing a hard capsule, a base portion 11 and 21 was held with hands such that the base portion 11 and 21 faces upwards while the pin portion 12 and 22 faces downwards to be immersed in the aqueous composition. Then, when each mold pin 10 and 20 was taken out from the each aqueous composition for preparing a hard capsule, each mold pin 10 and 20 maintained the status quo for 10 seconds after each mold pin 10 and 20 was completely taken out, and then inverted such that the base portion 11 and 21 faces downwards and the pin portion 12 and 22 faces upwards. The prepared hard capsule (hence, the body and the cap) may have non-uniform film thickness for the following reasons: when each mold pin 10 and 20 is taken out from the each aqueous composition for preparing a hard capsule, the coated aqueous composition on the mold pin 10 and 20 may slightly sag towards the bottom, and when the mold pin 10 and 20 is inverted at this point, the sagged portion may move to one portion. When the sagged portion is dried, the portion becomes thick and the thickness of the film of the hard capsule becomes non-uniform.

Evaluation Example

Gel strength of the aqueous compositions for preparing a hard capsule prepared in Examples 1 to 4 and Comparative Examples 1 and 2; and tensile strength and hardness of the flat films prepared in Examples 1 to 4, and Comparative Examples 1 and 2 were measured, and the results are shown in Table 2 below. Also, thicknesses of portions of the hard capsules (hence, capsule films) prepared in Examples 1 to 4 and Comparative Example 1 were measured by using the method described below and the results are shown in Table 3 below. Also, a ratio of a maximum thickness to a minimum thickness of the body and the cap and a ratio of a maximum thickness to a minimum thickness of the entire hard capsule were calculated and the ratios are shown in Table 4 below.

(Evaluation Method of Gel Strength of Aqueous Composition for Preparing Hard Capsule)

The each aqueous composition for preparing a hard capsule maintained at a temperature of 60° C. was cooled to room temperature (about 25° C.) and then gelled. Then, Texture Analyser (Brookfield, CT3-4500, Probe No: TA10) was used to measure strength of a gel formed from the each aqueous composition for preparing a hard capsule. However, the aqueous compositions for a hard capsule prepared in Comparative Examples 1 and 2 did not have sufficient gelation ability and thus, gel could not be formed and the gel strength could not be measured.

(Evaluation Method of Tensile Strength and Hardness of Flat Film)

Each of the flat films was cut into a size of 1 cm×10 cm and then LLOYD Instrument testing machine (LRX plus, available from LLOYD Instrument, UK) was used to measure tensile strength of the flat film. Also, each of the flat film was cut into a size of 4 cm×5 cm and then Texture Analyzer (Brookfield, CT3-4500, Probe No. TA-39) was used to measure hardness of the flat film.

(Measuring Method of Thickness of Hard Capsule)

Thicknesses of the hard capsules prepared in Examples 1 to 4 and Comparative Example 1 were measured for each portion by using a dial gauge (available from Mitutoyo, ID-C112XB).

TABLE 2

| | Gel strength of aqueous composition for preparing hard capsule (g) | Properties of flat film | |
|---|---|---|---|
| | | Tensile strength (N/mm$^2$) | Hardness (g) |
| Example 1 | 120 | 66 | 3,250 |
| Example 2 | 118 | 64 | 3,190 |
| Example 3 | 115 | 60 | 3,205 |
| Example 4 | 116 | 60 | 3,120 |
| Comparative Example 1 | Not measurable | 52 | 2,640 |
| Comparative Example 2 | Not measurable | 51 | 2,570 |

TABLE 3

| | Thickness of each portion of hard capsule (μm) | | | | | | | |
|---|---|---|---|---|---|---|---|---|
| | Body | | | | Cap | | | |
| | Top portion | Shoulder portion | Dome portion | Cutting edge portion | Top portion | Shoulder portion | Dome portion | Cutting edge portion |
| Example 1 | 165 | 75~80 | 105~111 | 96~101 | 150 | 80~85 | 110~115 | 95~100 |
| Example 2 | 148 | 78~84 | 110~115 | 97~103 | 148 | 75~82 | 105~111 | 95~102 |
| Example 3 | 165 | 80~90 | 111~115 | 95~99 | 155 | 70~79 | 102~105 | 97~105 |
| Example 4 | 170 | 78~95 | 107~112 | 98~104 | 140 | 75~85 | 108~112 | 100~105 |
| Comparative Example 1 | 205 | 79~110 | 105~130 | 83~101 | 170 | 60~120 | 90~125 | 85~112 |
| Comparative Example 2 | Not measurable | | | | | | | |

TABLE 4

| | Thickness ratio (maximum thickness/ minimum thickness) | |
|---|---|---|
| | Body | Cap |
| Example 1 | 2.2 | 1.9 |
| Example 2 | 1.9 | 2.0 |
| Example 3 | 2.1 | 2.2 |
| Example 4 | 2.2 | 1.9 |
| Comparative Example 1 | 2.6 | 2.86 |

TABLE 4-continued

| | Thickness ratio (maximum thickness/ minimum thickness) | |
|---|---|---|
| | Body | Cap |
| Comparative Example 2 | Not measurable | |

Referring to Table 2 above, the flat films prepared in Examples 1 to 4 have higher tensile strength and hardness compared to the flat films prepared in Comparative Examples 1 and 2.

Referring to Table 3 above, the hard capsules prepared in Example 1 to 4 have excellent thickness uniformity compared to the hard capsule prepared in Comparative Example 1.

While the present invention has been particularly shown and described with reference to exemplary embodiments thereof, it will be understood by those of ordinary skill in the art that various changes in form and details may be made therein without departing from the spirit and scope of the present invention as defined by the following claims.

EXPLANATION OF REFERENCE NUMERALS DESIGNATING THE MAJOR ELEMENTS OF THE DRAWINGS

10: MOLD PIN FOR BODY
11, 21: BASE PORTION
12, 22: PIN PORTION\
20: MOLD PIN
100: HARD CAPSULE
110: BODY
111, 121: TOP PORTION
112, 122: A SHOULDER PORTION
113, 123: DOME PORTION
114, 124: CUTTING EDGE PORTIONS
120: CAP

The invention claimed is:

1. A gastric hard capsule comprising:
   water-soluble cellulose ether;
   about 0.5 parts by weight to about 1.5 parts by weight of a gelation agent based on 100 parts by weight of the water-soluble cellulose ether; and
   about 0 parts by weight to about 0.3 parts by weight of a gelation aid based on 100 parts by weight of the water-soluble cellulose ether,
   wherein the cellulose ether refers to a cellulose derivative prepared by etherifying a hydroxy group of cellulose by using an etherifying agent,
   wherein the water-soluble cellulose ether comprises hydroxypropyl methylcellulose (HPMC), hydroxyethyl methylcellulose (HEMC), methylcellulose (MC), or a mixture of two or more of these,
   wherein the hard capsule is prepared from an aqueous composition comprising water, an alcohol that is at least one of methanol, ethanol, isopropanol, or butanol, the water-soluble cellulose ether, the gelation agent, and optionally, the gelation aid, wherein the aqueous composition comprises 5 wt % to 30 wt % of the alcohol, and is prepared by a process including mixing the water and the alcohol to prepare an aqueous alcohol solution, heating the aqueous alcohol solution to a temperature of 40° C. to 70° C., dissolving the water-soluble cellulose ether in the heated aqueous alcohol solution to prepare a cellulose ether solution, aging the cellulose ether solution, and adding the gelation agent and optionally, the gelation aid, to the cellulose ether solution,
   wherein the hard capsule comprises a body, and a cap that seals the body, and a ratio of the maximum thickness to the minimum thickness of the body is in a range of 1.9 to 2.5 and a ratio of the maximum thickness to the minimum thickness of the cap is in a range of 1.9 to 2.5,
   wherein the maximum thickness of the body is measured at a top portion of the body and the minimum thickness of the body is measured at a shoulder portion of the body,
   wherein the maximum thickness of the cap is measured at a top portion of the cap and the minimum thickness of the cap is measured at a shoulder portion of the cap,
   the term "minimum thickness" refers to a thickness having the minimum value among thicknesses of the body or the cap of the hard capsule at all measurable locations, and the term "maximum thickness" refers to a thickness having the maximum value among thicknesses of the body or the cap of the hard capsule at all measurable locations.

2. The gastric hard capsule of claim 1, wherein
   the body and the cap each includes a top portion, a shoulder portion, a dome portion, and a cutting edge portion, wherein
   thicknesses for portions of the body and the cap are each independently, the top portion from about 130 μm to about 180 μm, the shoulder portion from about 50 μm to about 100 μm, the dome portion from about 100 μm to about 120 μm, and the cutting edge portion from about 90 μm to about 110 μm.

3. The gastric hard capsule of claim 1, wherein the gelation agent comprises carrageenan, gellan gum, xanthan gum, pectin, or a mixture of two or more of these.

4. The gastric hard capsule of claim 1, wherein the gelation aid comprises potassium chloride, potassium acetate, calcium chloride, or a mixture of two or more of these.

5. The gastric hard capsule of claim 1, further comprising about 0 parts by weight to about 5.0 parts by weight of other additives based on 100 parts by weight of the water-soluble cellulose ether.

6. The gastric hard capsule of claim 5, wherein the other additives comprise a plasticizer, an emulsifier, or a mixture of these.

7. The gastric hard capsule of claim 1, wherein the aqueous composition comprises about 5 wt % to 15 wt % of the alcohol.

8. The gastric hard capsule of claim 1, wherein the aging of the ether cellulose solution includes aging at a temperature of 40° C. to 70° C. for 2 to 12 hours.

9. The gastric hard capsule of claim 1 having a tensile strength in a range of 60 N/mm$^2$ to 66 N/mm$^2$.

10. The gastric hard capsule of claim 9 having a hardness in a range of 3120 grams to 3250 grams.

11. The gastric hard capsule of claim 9 having a ratio of the maximum thickness to the minimum thickness of the body in a range of 1.9 to 2.2 and a ratio of the maximum thickness to the minimum thickness of the cap in a range of 1.9 to 2.0.

* * * * *